US008812250B2

(12) United States Patent
Hill et al.

(10) Patent No.: US 8,812,250 B2
(45) Date of Patent: Aug. 19, 2014

(54) ION MOBILITY SPECTROMETRY SYSTEMS AND ASSOCIATED METHODS OF OPERATION

(75) Inventors: Herbert H. Hill, Pullman, WA (US); Eric J. Davis, Pullman, WA (US)

(73) Assignee: Washington State University, Pullman, WA (US)

( * ) Notice: Subject to any disclaimer, the term of this patent is extended or adjusted under 35 U.S.C. 154(b) by 336 days.

(21) Appl. No.: 13/163,568

(22) Filed: Jun. 17, 2011

(65) Prior Publication Data

US 2012/0004862 A1 Jan. 5, 2012

Related U.S. Application Data

(60) Provisional application No. 61/356,459, filed on Jun. 18, 2010.

(51) Int. Cl.
*G06F 19/00* (2011.01)
(52) U.S. Cl.
USPC .......................................................... 702/28
(58) Field of Classification Search
USPC .......................................................... 702/28
See application file for complete search history.

(56) References Cited

U.S. PATENT DOCUMENTS

| | | | | |
|---|---|---|---|---|
| 4,988,628 A * | 1/1991 | Nanji | 436/173 |
| 5,426,056 A * | 6/1995 | Nacson | 436/91 |
| 7,071,465 B2 * | 7/2006 | Hill et al. | 250/286 |
| 7,414,242 B2 * | 8/2008 | Hill et al. | 250/288 |
| 7,417,222 B1 * | 8/2008 | Pfeifer et al. | 250/282 |
| 7,705,296 B2 * | 4/2010 | Wu | 250/282 |
| 2005/0253061 A1 * | 11/2005 | Cameron et al. | 250/287 |
| 2008/0173809 A1 * | 7/2008 | Wu | 250/283 |
| 2009/0078861 A1 * | 3/2009 | Hill et al. | 250/282 |
| 2009/0236514 A1 * | 9/2009 | Renner | 250/282 |
| 2010/0044557 A1 * | 2/2010 | Prox et al. | 250/281 |
| 2010/0200746 A1 * | 8/2010 | Osgood et al. | 250/282 |
| 2010/0224776 A1 * | 9/2010 | Wu | 250/282 |
| 2011/0006196 A1 * | 1/2011 | Boyle et al. | 250/281 |
| 2011/0266428 A1 * | 11/2011 | Scott et al. | 250/281 |
| 2011/0266436 A1 * | 11/2011 | Scott et al. | 250/287 |
| 2012/0025070 A1 * | 2/2012 | Miller et al. | 250/287 |
| 2012/0068061 A1 * | 3/2012 | Griffin et al. | 250/282 |
| 2012/0126109 A1 * | 5/2012 | Wu | 250/282 |

OTHER PUBLICATIONS

William F. Siems,* Ching Wu, Edward E. Tarver, and Herbert H. Hill, Jr. Measuring the Resolving Power of Ion Mobility Spectrometers; Anal. Chem. 1994,66, 4195-4201.*
Abu B. Kanu, Molly M. Gribb, and Herbert H Hill Jr. Predicting Optimal Resolving Power for Ambient Pressure Ion Mobility Spectrometry (IMS); Anal Chem. 2008 Sep. 1; 80(17): 6610-6619. doi:10.1021/ac8008143.*

* cited by examiner

*Primary Examiner* — Sujoy Kundu
*Assistant Examiner* — Alvaro Fortich
(74) *Attorney, Agent, or Firm* — Liang IP, PLLC

(57) ABSTRACT

Ion mobility spectrometry systems, devices, and associated methods of operation are disclosed herein. In one embodiment, a method for performing ion mobility spectrometry includes ionizing a sample in gas phase and applying an electric field to the ionized sample in the gas phase, thereby moving the ionized sample along a drift region. The applied electric field has a plurality of strength values with respect to time, and the individual strength values being generally constant during a corresponding period of time. The method further includes detecting an ion intensity and a drift time of the ionized sample moving through the drift region under the applied electric field with the plurality of strength values.

23 Claims, 9 Drawing Sheets

US 8,812,250 B2

ION MOBILITY SPECTROMETRY SYSTEMS AND ASSOCIATED METHODS OF OPERATION

STATEMENT REGARDING FEDERALLY SPONSORED RESEARCH

This work was supported in part by National Science Foundation grant #0731306. The government has certain rights in this work.

CROSS-REFERENCE TO RELATED APPLICATION(S)

This application claims priority to U.S. Provisional Application No. 61/356,459, filed on Jun. 18, 2010, the disclosure of which is incorporated herein by reference in its entirety.

TECHNICAL FIELD

The present disclosure is related generally to ion mobility spectrometry systems, devices, and associated methods of operation.

BACKGROUND

Ion Mobility Spectrometry ("IMS") is an analytical technique commonly used in searching for explosives, narcotics, and other trace contraband. As a result, IMS systems need to distinguish between closely-related chemical compounds and reliably respond when an illicit material is present. However, IMS systems typically have a lower resolution when compared to mass spectrometry ("MS") or chromatography. Hybrid ion mobility-mass spectrometry systems ("IMMS") having an ion mobility spectrometer coupled to a mass spectrometer can have higher resolutions than conventional IMS systems. However, field-portable IMS systems require a small instrument footprint. As a result, mass spectrometers with bulky vacuum systems are not feasible for such an application. Accordingly, there is a need to improve the ability of field-portable IMS systems to resolve closely related chemical compounds.

DETAILED DESCRIPTION

Figure 1A:
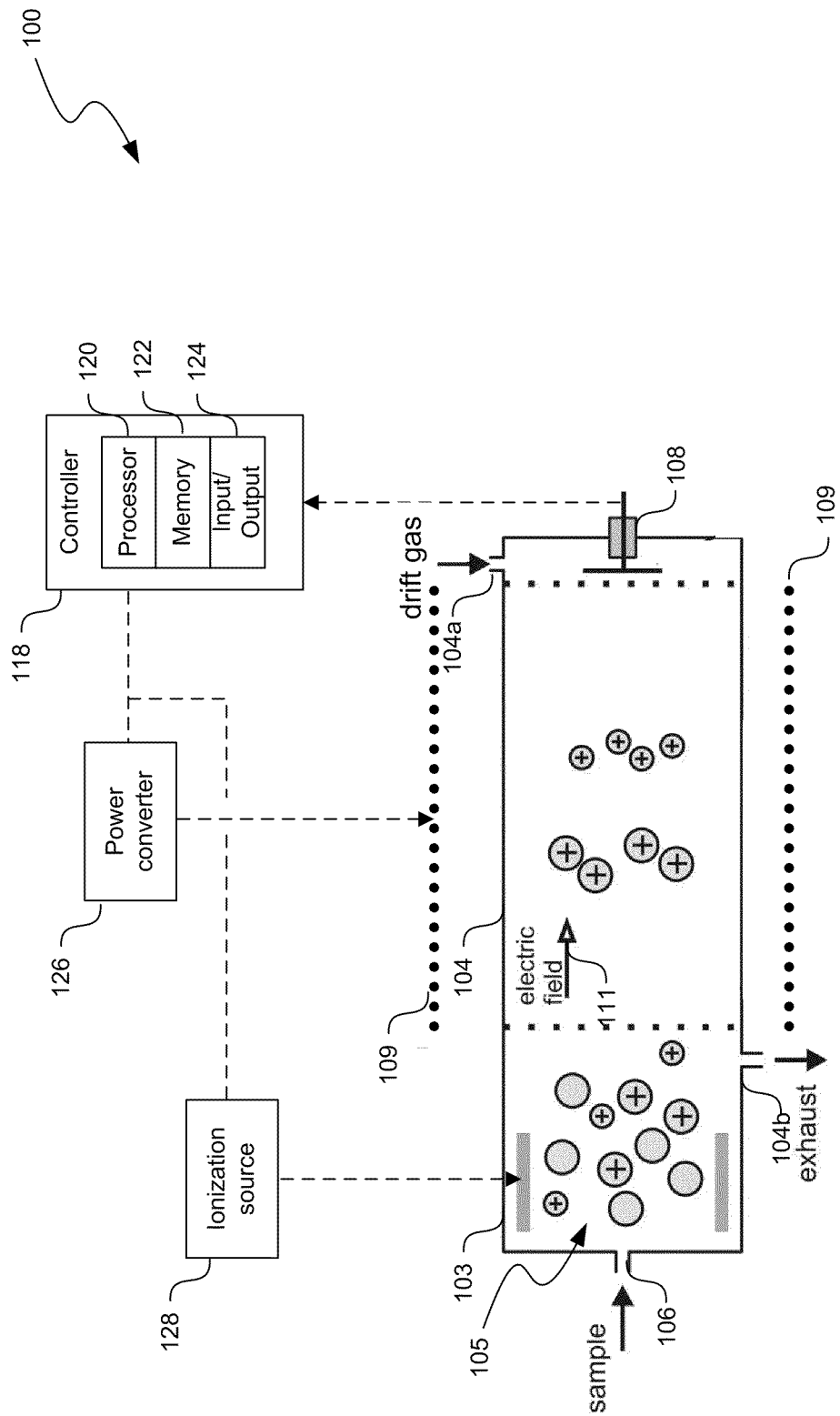
FIG. 1A is a schematic diagram of an IMS system configured in accordance with embodiments of the present technology.

Various embodiments of ion mobility spectrometry systems, devices, and associated methods of operation are described below. The term "ion mobility spectrometry" is used throughout to refer to an analytical technique for separating and identifying ionized molecules based on mobility in a drift medium. Example IMS systems are described below with particular operating parameters for illustration purposes only. Other embodiments of IMS systems in accordance with the present technology may also operate at low pressures (e.g., from about 1 mbar to about 20 mbar), at high pressure (e.g., 1013 mbar), at low temperatures (e.g., room temperature), at high temperatures (e.g., about 100° C. to about 200° C.), with different types of drift media (e.g. liquids, supercritical gases, and gases) with different compositions of drift medium (e.g., helium, nitrogen, argon, carbon dioxide, etc.), with different drift tube designs, and/or at other suitable conditions. A person skilled in the relevant art will also understand that the technology may have additional embodiments, and that the technology may be practiced without several of the details of the embodiments described below with reference to FIGS. 1A-7.

Studies have been conducted to investigate the relationship between various IMS operating parameters and resolving power of IMS systems. The investigated operating parameters include pressure, temperature, drift medium selection, drift tube design, and voltage. The studies show that these parameters each have a distinct effect on resolving power of an IMS system. For example, studies have shown that pressure tends to increase resolving power, but also increases ion-neutral clustering. Temperature decreases clustering but also decreases resolving power. Thus, IMS devices are often operated at ambient pressure and at temperatures between 100° C. and 200° C. in order to achieve good resolving power with acceptable level of clustering. Increased temperatures also help to reduce formation of contaminants in IMS systems and thus reduce clear-down time. In another example, studies have also shown that a longer tube tends to increase resolving power but reduces signal strength when compared to a shorter tube. In a further example, studies have shown that the selection of drift medium can significantly alter the separation characteristics of ion mobility by altering the polarizability of the drift medium, and thus changing ion-neutral interactions. These changed interactions can facilitate the separation of one pair of ions while inhibiting separation of other ions.

Even though pressure, temperature, drift tube design, and drift medium selection can affect resolving power of IMS systems, these parameters cannot be easily altered during operation. Instead, voltage is a variable that may be readily varied during operation. However, studies have shown that an optimal drift voltage used to achieve high resolving power often results in low signal-to-noise ratios. As a result, non-optimal drift voltages are commonly used to achieve lower detection limits. At low drift voltages, the peaks of ions with low mobility are often broad with low signal-to-noise ratios. On the other hand, at high voltages, the resolving power of ions with high mobility are sacrificed. Thus, an elution difficulty exists in separating ions with a wide range of mobility values in a single run.

Currently, the inventors are not aware of any solutions to the foregoing elution difficulty of conventional IMS systems. Though it is possible to select IMS operating parameters to favor increased separation of particular ions (e.g., slow or fast ions), conventional techniques cannot separate both types of ions simultaneously. It is believed that an optimal drift voltage exists for an ion with a particular mobility value to achieve the highest possible resolving power. As discussed in more detail below, several embodiments of the present technology can improve peak capacity and increase resolving power of IMS systems by changing a drift voltage when applying ion mobility spectrometry.

FIG. 1A is a schematic diagram of an IMS system 100 configured in accordance with embodiments of the present technology. As shown in FIG. 1A, the IMS system 100 can include an ionization section 103, a drift tube 104, a detector 108, a controller 118, a power converter 126, and an ionization source 128 operatively coupled to one another. Even though only the foregoing components are shown in FIG. 1A, in other embodiments, the IMS system 100 can also include pressure controllers, temperature controllers, and/or other suitable components.

The power converter 126 and the ionization source 128 can be configured to supply a voltage and/or current to the drift tube 104 and the ionization section 103, respectively. The power converter 126 and the ionization source 128 can individually include a buck, a boost, an inverting, a flywheel, and/or other suitable types of voltage and/or current power converter. In the illustrated embodiment, the power converter 126 and the ionization source 128 are shown as separate components. In other embodiments, the power converter 126 and the ionization source 128 may be integrated into one component.

The ionization section 103 can include a reaction zone 105 coupled to a sample inlet 106. In operation, a sample (with or without a carrier gas) may be injected into the reaction zone 105 via the sample inlet 106. The injected sample can then be at least partially ionized in the reaction zone 105 before flowing toward the drift tube 104. In the illustrated embodiment, the ionization section 103 is directly coupled to the drift tube 104 to form a unitary body. In other embodiments, the ionization section 103 may be coupled to the drift tube 104 via pipes, tubes, and/or other suitable conduits.

The drift tube 104 can include a drift medium inlet 104a, a drift medium outlet 104b, and an electric field generator 109 coupled to the power converter 126. In operation, the power converter 126 applies a voltage and/or current bias to the electric field generator 109, which in turn generates an electric field 111 in the drift tube 104. In one embodiment, the electric field 111 can be generally uniform in the drift tube 104. In other embodiments, the electric field 111 may have other suitable distribution profiles. Even though the electric field generator 109 is shown in FIG. 1 as two parallel series of electrodes spaced apart from the drift medium inlet and outlet 104a and 104b, in other embodiments, the electric field generator 109 may include two plates, a radio frequency generators, and/or other suitable components capable of generating an electric field in the drift tube 104.

The detector 108 can include a Faraday plate and/or other suitable components for detecting ions flowing through the drift tube 104. In one embodiment, ions are recorded at the detector 108 from the fastest to the slowest to generate a response signal characteristic for a chemical composition of the measured sample. In other embodiments, ions may be recorded and/or detected via other suitable techniques.

The controller 118 can include a processor 120 coupled to a memory 122 and an input/output component 124. The processor 120 can include a microprocessor, a field-programmable gate array, and/or other suitable logic devices. The memory 122 can include non-transitory volatile and/or non-volatile media (e.g., ROM; RAM, magnetic disk storage media; optical storage media; flash memory devices, and/or other suitable storage media) and/or other types of computer-readable storage media configured to store data received from, as well as instructions for, the processor 120 (e.g., instructions for performing the methods discussed below with reference to FIGS. 1B and 1C). The input/output component 124 can include a display, a touch screen, a keyboard, a mouse, and/or other suitable types of input/output devices configured to accept input from and provide output to an operator.

In certain embodiments, the controller 118 can include a personal computer operatively coupled to the other components of the IMS system 100 via a communication link (e.g., a USB link, an Ethernet link, a Bluetooth link, etc.) In other embodiments, the controller 118 can include a network server operatively coupled to the other components of the IMS system 100 via a network connection (e.g., an internet connection, an intranet connection, etc.) In further embodiments, the controller 118 can include a process logic controller, a distributed control system, and/or other suitable computing frameworks.

As discussed in more detail below with reference to FIGS. 2A and 2B, embodiments of the IMS system 100 may at least reduce the impact of the ion elution difficulty discussed above by adjusting a strength of the electric field (e.g., by sweeping voltages) in the drift tube 104, referred to hereinafter as voltage-sweep ion mobility spectrometry ("VSIMS"). As discussed below, such a technique can increase a peak capacity of ion mobility spectrometry when compared to conventional IMS techniques. In addition to increased the peak capacity, the voltage sweep can be programmed to operate under target voltage conditions for individual drift time. As a result, individual peaks in an IMS spectrum may be detected under a voltage with increased resolving power. VSIMS may also be used to determine the mobility of a particular ion at a plurality of voltage levels, and thus producing an average mobility value over a range of voltage levels.

Before discussing the details of VSIMS, theoretical background of the IMS technique is discussed below for illustrating the foundation of VSIMS. The IMS techniques analyze drift times typically by calculating reduced mobility values (in $cm^2V^{-1}s^{-1}$), which may be adjusted with respect to standard temperature and pressure. Reduced mobility ($K_o$) is defined as follows:

$$K_o = \frac{L^2}{Vt_d} \frac{P}{760} \frac{273.15}{T} \qquad \text{[Equation 1]}$$

where L is the length of the drift tube (in cm), V is the voltage across the drift tube, $t_d$ is the drift time of the ion (in seconds), P is the pressure, and T is the temperature of the drift tube.

Resolving power can be used to compare the relative ability of two IMS systems to separate similar compounds. As used hereinafter, resolving power in IMS is defined as follows:

$$R_p = \frac{t_d}{FWHM} \quad \text{[Equation 2]}$$

where R is the resolving power of an IMS system, $t_d$ is the drift time of a peak, and FWHM is the full width at half of the maximum of an IMS spectral peak. Without being bound by theory, it is believed that the resolving power of an IMS system under varying conditions (typically referred to as conditional resolving power ($R_c$)) can be described by the following, assuming that the only factors affecting the resolving power are gate pulse width and simple diffusion:

$$R_c = \frac{1}{\sqrt{\left(\frac{760}{273.15}\right)^2 \frac{t_g^2 K_o^2 T^2 V^2}{L^4 P^2} + \frac{16 k_B T \ln 2}{qV}}} \quad \text{[Equation 3]}$$

where $t_g$ is the pulse width of the ion gate, $K_o$ is the reduced mobility of the ion of interest, T is the temperature, V is the voltage across the drift space, L is the length of the drift tube, P is the pressure of the system, $k_B$ is the Boltzmann constant, and q is the elementary charge. An optimal drift voltage can be calculated by taking the derivative of Equation [3] with respect to voltage, and thus:

$$V_{opt} = 0.0395 \left[\frac{L^4 P^2}{t_g^2 K_o^2 T}\right]^{1/3} \quad \text{[Equation 4]}$$

Equations [1] and [4] may be combined and solved for drift time to produce an optimal drift time at a particular voltage as follows:

$$t_{opt} = \frac{273.15}{760} \frac{t_g}{0.0395 T} \sqrt{\frac{TV}{0.0395}} \quad \text{[Equation 5]}$$

As shown in Equation [5], the optimum drift time is independent of length and pressure of a drift tube, providing a simple curve which may be applied to a drift tube to achieve similar results.

Figure 1B:
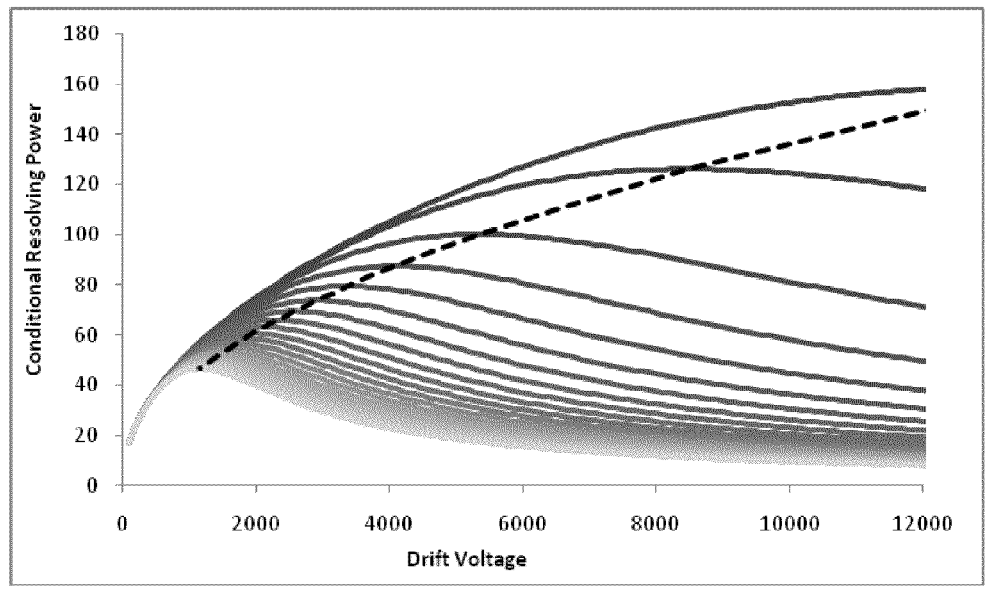
FIG. 1B is a plot of conditional resolving power (Rc) versus voltage over a range of 0 to 12,000 volts in accordance with embodiments of the present technology.
Figure 1C:
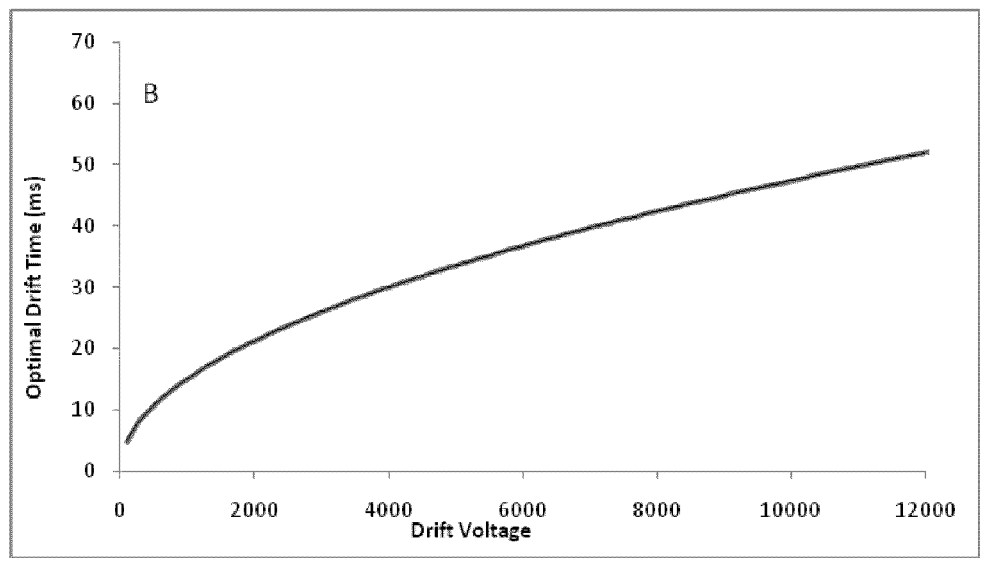
FIG. 1C is a plot of expected optimal drift time versus voltage in accordance with embodiments of the present technology.

Theoretical results of Equations [3] and [4] are shown in FIG. 1B. The curves represent the resolving power predicted by Equation [3], plotted versus drift voltage in the range of 0 to 12,000 volts. The dashed line represents the resolving power predicted by Equation [4], intersecting each curve at the maximum predicted value (i.e., expected optimal voltage). These values correspond to the drift times predicted by Equation [5] and are shown in FIG. 1C. As shown in FIGS. 1B and 1C, as the drift voltage is increased, the IMS spectrum can be monitored at the drift time according to the curve in FIG. 1C to maintain a target resolving power of the IMS system 100 (FIG. 1A), as discussed below with reference to FIGS. 2A and 2B.

Figure 2A:
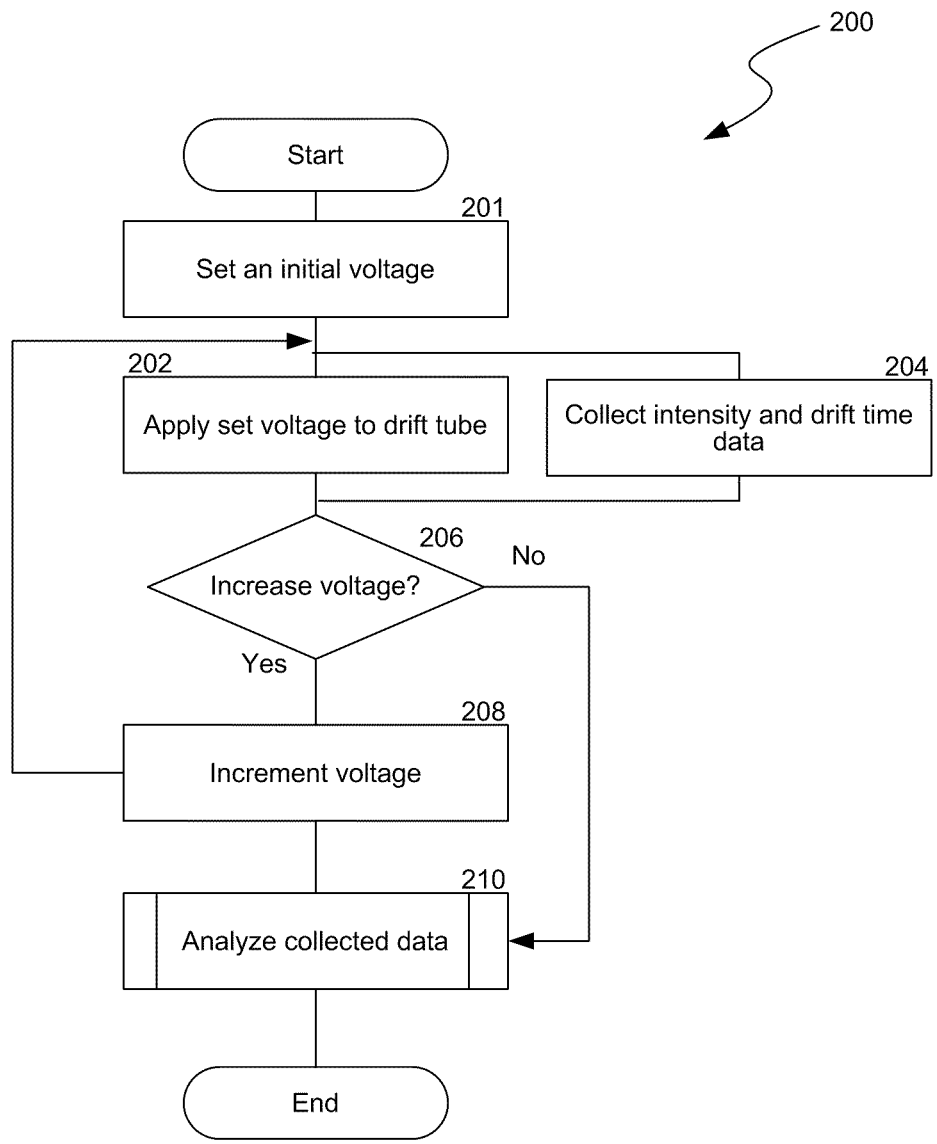
FIG. 2A is a flowchart showing a method for operating the IMS system in FIG. 1A in accordance with embodiments of the present technology.

FIG. 2A is a flowchart showing a method 200 for operating the IMS system in FIG. 1A in accordance with embodiments of the present technology. Various embodiments of the method 200 may be implemented as a computer program, procedure, or process written as source code in a conventional programming language, such as C, C+, C++, C# etc., and may be presented for execution by the processor 120 (FIG. 1A) of the controller 118 (FIG. 1A). The various implementations of the source code and object byte codes may be stored in the memory 122 (FIG. 1A) or on a computer-readable storage medium (not shown). Even though the method 200 is described below as applied in the IMS system 100 of FIG. 1A, embodiments of the method 200 may be implemented in other suitable IMS systems.

As shown in FIG. 2A, an initial stage of the process can include setting an initial scanning voltage at stage 201. The initial scanning voltage can be about 5 volts, 50 volts, 500 volts, or any other suitable voltages based on particular requirements of the application. The initial scanning voltage may be set by accepting an input form an operator via the input/output component 124 (FIG. 1A), may be set by default in the memory 122 (FIG. 1A), and/or may be set by other suitable techniques.

Another stage 202 of the process can include applying the set voltage to the drift tube 104 (FIG. 1A), and in stage 204 collecting intensity from, for example, the detector 108 (FIG. 1A) and drift time data. The applied set voltage can be generally constant over a set scan period (e.g., 25 ms or other suitable periods). In certain embodiments, the collected intensity and drift time data along with the scanning voltage may be stored as a matrix in the memory 122 of the controller 118 (FIG. 1A). In other embodiments, the collected intensity, the drift time data, and the scanning voltage may be plotted as a three dimensional graph and/or stored in other suitable format.

A subsequent stage includes a decision block 206, in which it is determined whether the voltage can be increased. In one embodiment, the voltage can be increased if the scan period has expired and a maximum voltage (e.g., 12,000 volts) has not been reached. In other embodiments, the determination may be based on other suitable criteria.

If the voltage can be increased, the process includes incrementing the voltage at stage 208. In one embodiment, the voltage may be incremented sequentially by a constant amount (e.g., 10 volts, 100 volts, or other suitable voltages). In another embodiment, the voltage may be incremented sequentially by a constant amount only over a select voltage range. In other embodiments, the voltage may be incremented by a variable amount. For example, in one embodiment, if the collected intensity and/or drift time data in the previous scan period are greater than a predetermined threshold, the voltage may be incremented by a first value; otherwise, the voltage may be incremented by a second value greater than the first value. In further embodiments, the voltage may be incremented by other suitable values.

Subsequent to incrementing the voltage, the process reverts to applying the set voltage (block 202) and collecting intensity and drift time data (block 204). If the voltage cannot be increased, the process proceeds to analyzing collected data at block 210. Embodiments of analyzing the collected data are discussed in more detail below with reference to FIG. 2B.

Figure 2B:
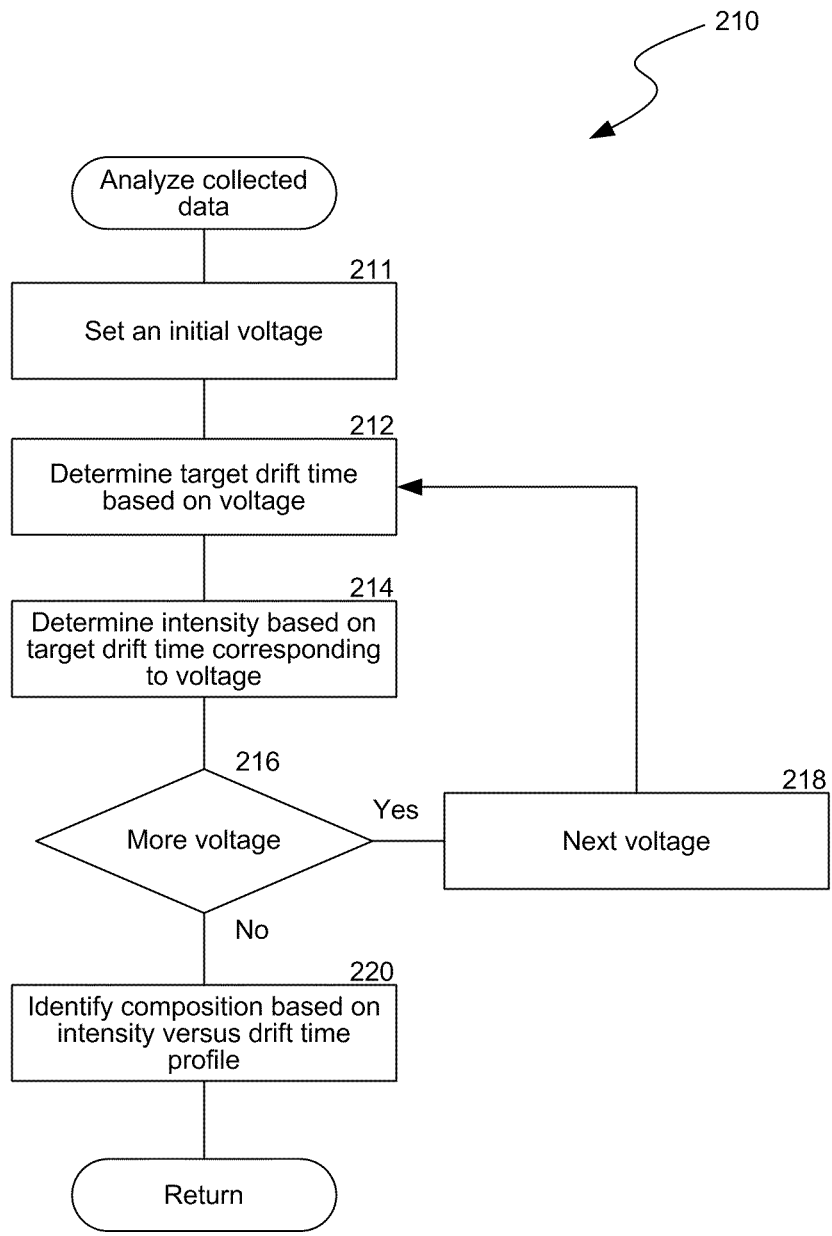
FIG. 2B is a flowchart showing a method of analyzing IMS data in accordance with embodiments of the present technology.

FIG. 2B is a flowchart showing a method 210 of analyzing IMS data in accordance with embodiments of the present technology. As shown in FIG. 2B, the initial stage of the process includes setting an initial analysis voltage (block 211). In one embodiment, the initial voltage for analysis can be equal to the initial scanning voltage in FIG. 2A. In other embodiments, the initial analysis voltage may be different from the initial scanning voltage.

Another stage of the process include determining a target drift time based on the set analysis voltage (block 212). In one embodiment, the target drift time can be calculated based on Equation [5] discussed above. In other embodiments, the target drift time can be offset by a factor from that calculated based on Equation [5]. In further embodiments, the target drift time may be calculated based on other suitable criteria.

Another stage of the process can include determine an intensity value for the determined target drift time corresponding to the set analysis voltage (block 214). In one embodiment, the intensity value may be determined by searching the stored matrix of collected intensity and drift time data. In other embodiments, the intensity value may be determined by applying linear interpolation, extrapolation, and/or other suitable data extraction techniques. In further embodiments, the intensity value may be determined graphically by superimposing at least one generated cursor (e.g., according to Equation [5]) over a two dimensional drift time verses voltage plot based on the collected data, as discussed in more detail with reference to FIGS. 4A and 4B.

A subsequent stage includes a decision block 216, in which it is determined whether additional voltage values should be processed. In one embodiment, additional voltage values exist when the present voltage value is less than the maximum scanning voltage. In other embodiments, the determination may be based on other suitable criteria.

If additional voltage values exist, the process proceeds to setting a new value to the analysis voltage (block 218) before reverts to determining a target drift time based on the analysis voltage with the new value (block 212). Otherwise, the process proceeds to identifying composition of a sample based on a profile between the determined intensity values and target drift time (block 220).

Even though particular embodiments of the methods 200 and 210 are discussed above, in other embodiments, the IMS system 100 of FIG. 1A may also be operated with additional and/or different stages. For example, in certain embodiments, the IMS system 100 may be initially operated based on the method 200 by applying a plurality of voltages to the drift tube 104. Subsequently, a determination may be made to select a particular voltage at which the resolving power satisfies a predetermined criterion. Subsequently, the IMS system 100 may be operated at the particular voltage without incrementing the voltage. In other embodiments, the IMS system 100 may be operated in other suitable manners.

EXPERIMENTS

Experiments were conducted in an IMS system according to several embodiments of the methods 200 and 210 discussed above. As discussed in more detail below, embodiments of the present technology may at least reduce the impact of the ion elution difficulty as compared to conventional techniques.

Reagents and Gases.

All compounds used were reagent grade, neat liquids provided by Sigma-Aldrich (St. Louis, Mo.). The compounds were diluted in methanol at concentrations with a vapor pressure of 1 Torr. Throughout the experiments, ultrahigh purity compressed air was used as the drift medium, with a flow rate of 1.5 L/min.

IMS Cell and Hardware.

The IMS drift tube used was built using a stacked-electrode design generally similar to that shown in FIG. 1A. The IMS drift tube had 22 stainless steel electrodes separated by alumina (99%, Bolt Technical Ceramics, Fairfield, N.J.) spacers to provide electrical isolation. Each resistor was connected to a neighbor through 1 MΩ resistors (±1%, Caddock: Riverside, Calif.), and a high voltage was applied to the first ring in the series, which provided an electric field gradient along the length of the drift tube.

An ion packet was selected through a Bradbury-Nielsen style ion gate, pulsed at 0.2 ms throughout experiments. The tube was heated by two 300 W Watlow cartridge heaters (St. Louis, Mo.), controlled using an Omega CN9000A temperature controller (Stamford, Conn.) to provide a generally constant temperature throughout the drift region of the IMS cell from room temperature up to 200° C. High voltage was provided using a Bertan 230 (Hauppauge, N.Y.) power supply, and a drift medium flow rate was controlled using an MKS M100B mass-flow controller (Andover, Mass.). Voltage and drift medium flows were controlled and maintained through the operating instructions of the IMS system. Ionization was achieved using a 50 mCi $^{63}$Ni foil affixed to a screen on the first ring in the reaction section. The high energy β particles from this foil provided initial ionization of the drift medium, after which samples were ionized through atmospheric pressure chemical ionization processes.

Sample Introduction.

Diluted samples were introduced with a pipette into 5 mL glass sample vials which were placed in a stainless steel sample chamber. This chamber was heated and had a controlled flow of air across the headspace of the sample vials. This carrier gas transported the vapor through a 300 μm heated fused-silica capillary transfer line into an electrode ring within the IMS system. The ring allowed a fused-silica capillary carrying the sample vapor to penetrate into the reaction section of the IMS immediately before the ion gate. The introduced sample vapors were carried by the drift medium towards the front of the IMS tube and the ionization source, where the sample was ionized.

A National Instruments NI PCI-MIO-16XE-10 DAQmx board (Austin, Tex.) provided analog input and output capabilities and allowed the control of the voltage and gas flow rates, as well as monitoring these values and collecting the IMS signal. Instructions were generated to allow operating the system in either a drift time mode, or in a voltage sweep mode. Such instructions can be stored in a computer readable medium generally similar to the memory 122 (FIG. 1A) and can be executed by the processor 120 (FIG. 1A).

In the drift time mode, the instructions provided the pulse sequence for the ion gate, as well as spectral averaging for the ion signal. The voltage sweep mode can be used to dynamically control the voltage applied to the IMS, while simultaneously controlling the pulsing sequence and signal averaging in the IMS system. The instructions were designed to increase the voltage by a set amount at a specific frequency. For example, in certain experiments, the voltage was increased by 10 volts/second, with a 25 ms scan time for the IMS, and 40 averages per point. For data output, the instructions allow selection of a specific drift time to monitor, or view the data as a two dimensional plot of drift time verses applied voltage.

Data analysis instructions generally similar to that shown in FIG. 2B were created to correspond to the voltage sweep mode, providing a two dimensional drift time verses voltage plot. By superimposing generated cursors over this plot, either the averaged IMS spectrum for any voltage or the voltage-sweep plot could be viewed at any selected drift time. In addition, from either of these plots, the resolving power of a single, selected peak, or the resolution of two adjacent peaks could be automatically calculated. The reduced mobility could also be calculated based on the spectrum, assuming the appropriate instrumental parameters (temperature, pressure, etc.). Finally, according to Equation [5], the drift time which was being monitored may be dynamically changed. Thus, for each voltage setting, the intensity of the spectrum was monitored at the expected optimal drift time based on Equation [5], as shown in FIG. 2B. This line can be calculated automatically according to the parameters input by a user, and changed dynamically if parameters are altered.

Voltage Sweep Parameters.

In order to investigate the effect of the voltage sweep scan rate on resolving power, several different voltage curves were studied. In selecting these values, the power supply limited the voltage resolution (volts/step) to a minimum of 5 volts, and the IMS gate pulsing allowed a update frequency below 40 Hz.

The voltage curve had an impact on the experimental time period, as well as the number of IMS averages obtained for each data point. For example, a voltage resolution of 10 volts, swept from 1,000 to 10,000 volts, with 40 IMS spectral averages per point had an experimental time of approximately 15 minutes. However, a voltage resolution of 5 volts in the same voltage range and the same number of IMS spectral averages took 30 minutes. Finally, a resolution of 20 Volts with 80 IMS averages required 15 minutes. However, an increased voltage resolution decreased the number of points available for the voltage sweep spectra, which resulted in a point-to-point averaging effect across theses spectra, reducing the apparent resolving power. Thus, a trade-off exists between the IMS averages (and thus signal-to-noise ratios), voltage resolution, and time of experiment. A parameter set used was 80 IMS spectral averages for each point, swept from 1,000 to 10,000 volts, with a voltage resolution of 10 volts; resulting in a 20 minute experimental period.

Separation Using Expected Optimal Drift Time/Voltage Curve.

Figure 3:
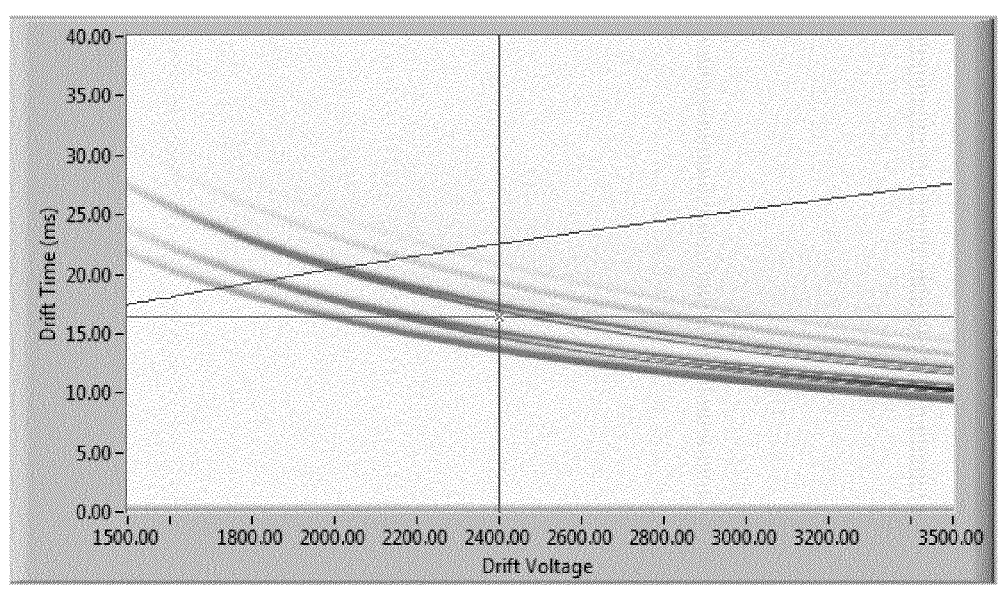
FIG. 3 is a screenshot of a two-dimensional drift time versus voltage plot for n-butylamine during an experiment in accordance with embodiments of the present technology.

FIG. 3 shows a screenshot of a two-dimensional drift time verses voltage plot for n-butylamine. The instructions allowed a user to select any voltage (using the vertical trace) to produce a drift time spectrum at that voltage. The horizontal trace allowed any drift time to be selected, producing a voltage sweep spectrum of intensity verses voltage, and the curved trace indicates the results of Equation [5] for the parameters used.

Figure 4:
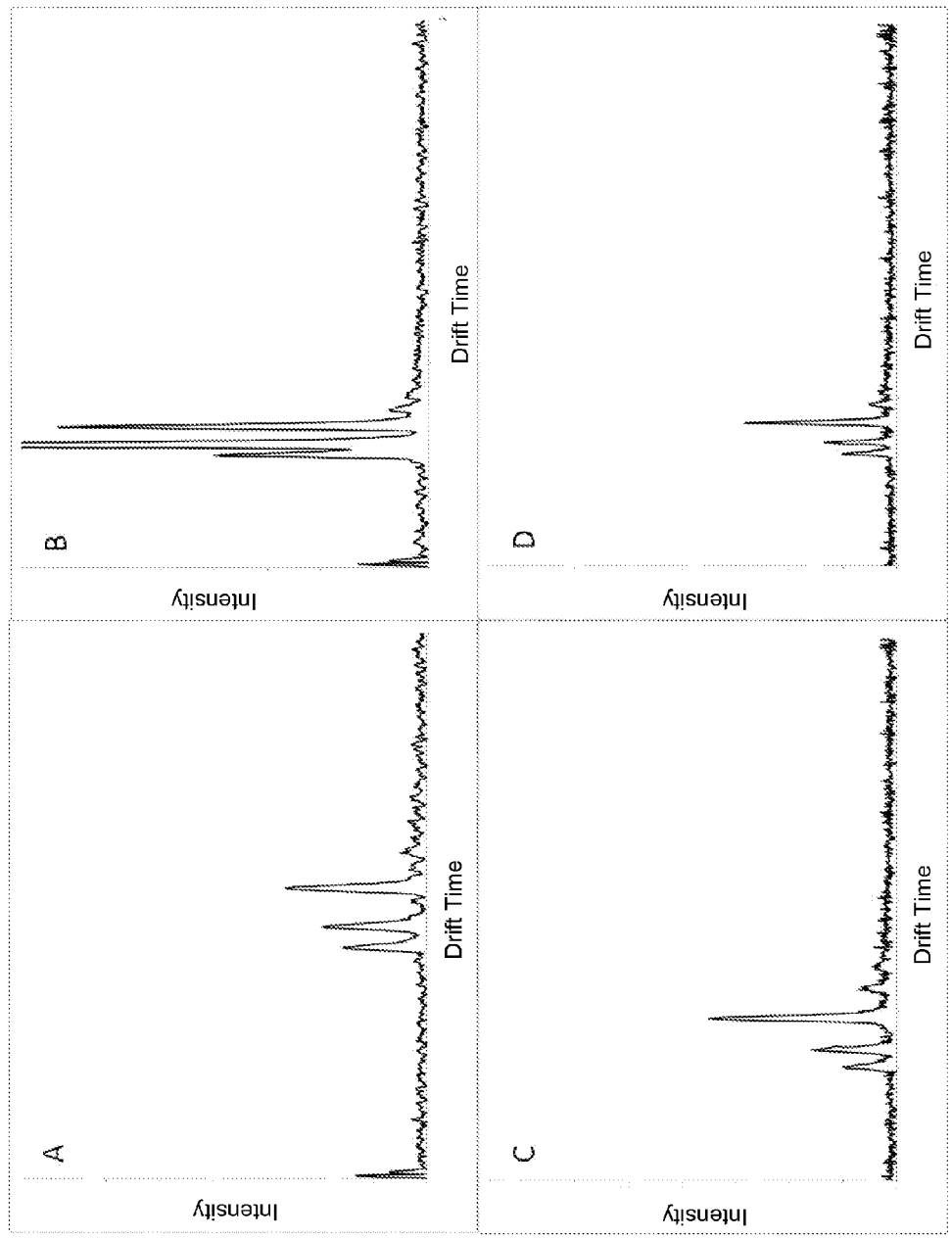
FIG. 4 shows four example ion mobility spectra of n-butylamine with different scanning voltages during an experiment in accordance with embodiments of the present technology.

FIG. 4 shows four spectrum plots of n-butylamine as obtained using the cursors discussed above. Plot A shows the mobility spectrum of n-butylamine with the IMS set to operate at the expected optimal voltage (1920 V, 180 V/cm). Plot B shows the mobility spectrum of n-butylamine at a voltage of 4032 V, or 400 V/cm. As shown in Plots A and B, a lower electric field produced a decreased signal, but facilitated separation. On the other hand, the higher field produced increased intensities by sacrificing resolution. Similar results were obtained when a faster drift time was selected for the voltage sweep spectrum displayed in Plot C. Both spectra used the same carrier gas flow rate and quantity of n-butylamine, but the spectrum obtained at 400 V/cm indicated a significantly higher signal-to-noise ratio (S/N)—S/N of 178 as compared to a S/N of 85 for the expected optimal voltage. However, the spectrum obtained at 180 V/cm provided a resolving power of 33, and the spectrum obtained at 400 V/cm had a resolving power of 25.

When the system was used in the voltage sweep mode, similar resolving powers were obtained. At the optimal drift time of 21.14 ms for n-butylamine, the voltage sweep (Plot C) provided a resolving power of 34. However, if the voltage and drift times were scanned according to Equation [5] (Plot D), the resolving power increased to a value of 49, near the conditional resolving power according to Equation [3].

The spectra displayed showed highly varied maximum intensity values. The highest signal intensity was found using the drift time mode at the highest voltage (4032V, 400 V/cm) (Plot B). However, the maximum signal observed in Plots A, C, and D, where the target voltages and drift times were utilized, was much lower. By decreasing the monitored drift time, the electric field is increased, resulting in an increased S/N ratio. Finally, the spectrum displayed in Plot D can be manipulated to higher signal intensity values through a multiplier. This shifted the selected drift time/voltage curve, as calculated by Equation [5], to values above or below that calculated theoretical maximum. By selecting a faster drift time, signal intensities can be increased in the same way as described for the voltage sweep mode.

Increased resolving power through the use of the simultaneous voltage and drift time variation technique was consistent regardless of the compound chosen. For example, 4-methyl-2-pentanone has a conditional resolving power of 61 under the conditions presented. In the drift time mode, a resolving power of 44 was obtained at the expected optimal voltage for a $K_0$ of 1.39 $cm^2V^{-1}s^{-1}$ (2296 V). In the voltage-sweep mode, a resolving power of 42 was obtained at the expected optimal drift time for this same $K_0$ (21.33 ms). Finally, under the target drift time/voltage conditions, a resolving power of 56 was obtained.

Table 1 contains the results of several compounds tested using this technique and lists the reduced mobility ($K_0$), the conditional resolving power ($R_c$), the Time Scan mode resolving power ($R_t$—obtained at the expected optimal voltage for the specified $K_o$), the voltage scan mode resolving power ($R_v$—obtained at the target drift time), the voltage sweep mode resolving power ($R_{opt}$) for the monomer peak of each compound, and the literature value for the reduced mobility of each compound ($K_{0,lit}$). The experimental data obtained by this technique gave an average $R_t$ that corresponds to 62% of the expected $R_c$, the $R_v$ gave an average of 57%, and the $R_{vopt}$ gave an average of 81% of $R_c$. Thus, the drift time variation technique provided a 31% increase in resolving power, 19% relative to the conditional resolving power.

| Compound | $K_o$ | $K_{olit}$ | $R_c$ | $R_t$ | $R_v$ | $R_{opt}$ |
|---|---|---|---|---|---|---|
| 2,4-lutidine | 1.95 | 1.95[1] | 60 | 40 | 35 | 48 |
| Di-tert-butylpyridine | 1.43 | 1.42[2,4] | 66 | 44 | 40 | 56 |
| Dimethyl-methylphosphonate | 1.91 | 1.91[1] | 60 | 24 | 31 | 43 |
| n-butylamine | 1.95 | 1.93[1] | 60 | 37 | 31 | 39 |
| Hexylamine | 1.69 | 1.68[1] | 63 | 40 | 35 | 52 |
| Cyclohexylamine | 1.81 | 1.81[20] | 61 | 43 | 31 | 50 |
| Heptylamine | 1.59 | 1.58[1] | 64 | 40 | 37 | 51 |
| Cycloheptylamine | 1.71 | 1.71[20] | 62 | 40 | 38 | 62 |
| Benzylamine | 1.75 | 1.73[1] | 62 | 38 | 31 | 47 |
| 2-Butanone | 2.03 | 2.00[1] | 59 | 33 | 36 | 51 |
| 4-Methyl-2-Pentanone | 1.39 | — | 61 | 44 | 42 | 56 |
| 2-Hexanone | 1.78 | 1.79[1] | 61 | 36 | 33 | 48 |
| Cyclohexanone | 1.85 | 1.84[1] | 61 | 35 | 34 | 48 |
| Cycloheptanone | 1.71 | — | 62 | 40 | 36 | 50 |
| Methyl Salicylate | 1.57 | 1.56[21] | 60 | 34 | 32 | 43 |

Separation of a Mixture.

Figure 5A:
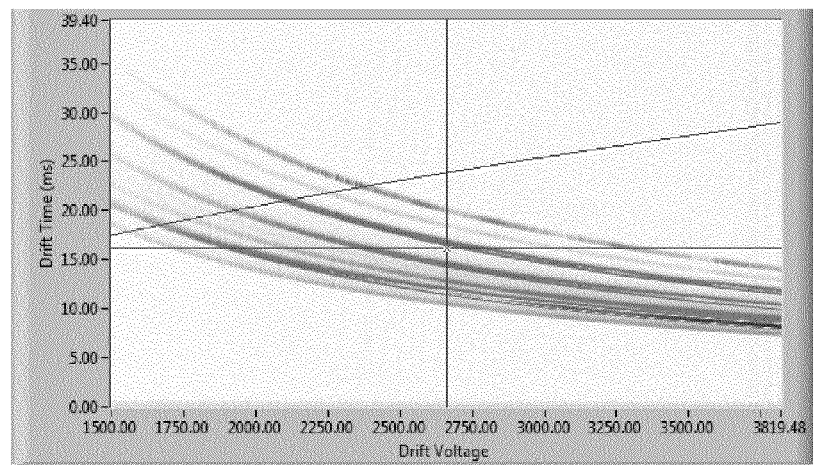
FIG. 5A is a screenshot of a two-dimensional drift time versus voltage plot for a mixture of 4-methyl-2-pentanone, 2-butanone, and heptylamine during an experiment in accordance with embodiments of the present technology.
Figure 5B:
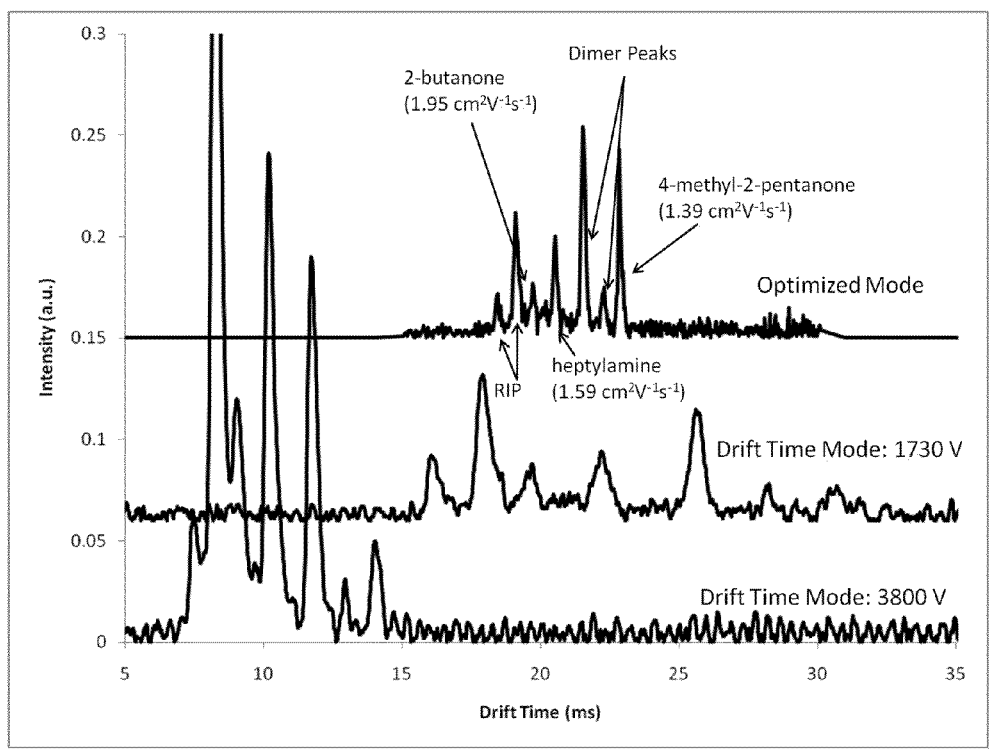
FIG. 5B is an intensity versus drift time plot based on data in FIG. 5A.

4-methyl-2-pentanone, 2-butanone, and heptylamine were combined and separated using VSIMS. FIG. 5A shows a two-dimensional drift time verses voltage intensity plot of this separation. Drift time mode IMS spectra of this separation were compared to the spectra in FIG. 5B. Peak identification shown in FIG. 5B was achieved through the use of reduced mobility values. At high field (3,800 volts, 350 V/cm) seven peaks are visible, but several were not baseline separated, especially noted between the two RIP peaks and between the RIP and the 2-butanone peaks. However, when drift time mode spectra were obtained under lower field conditions (1,730 V, 160 V/cm) for a $K_o$ of 1.95 $cm^2V^{-1}s^{-1}$, the peaks were well-separated, but with a loss in signal-to-noise ratio, as the 4-methyl-2-pentanone peak had an intensity value very close to the limit of detection ("LOD") for this instrument (e.g., the intensity of the 4-methyl-2-pentanone peak was 0.015 nA, the LOD was 0.012 nA).

When the voltage sweep mode was used, all seven peaks were resolved. In addition, in the voltage sweep mode the intensities of the peaks were much more uniform across the mobility range. It is believed that such an effect is due to the increased voltage at which the longer-drifting peaks were measured, resulting in increased signal for these peaks that are often difficult to detect at low voltages (as seen in the 1730 V spectrum).

Voltage-Sweep Parameters.

The effects of scan time on the voltage-sweep spectra were studied. Voltage sweep spectra were obtained for three condition sets: 'a short method' using 20 averaged IMS spectra per point and 20 volt increments, with an experimental period of about 7 minutes. A 'Medium method' used 80 averaged IMS spectra per point and 10 volt increments, with an experimental period of about 25 minutes, and a 'Long method' used 300 averaged IMS spectra per point and 5 volt increments, with an experimental period of just over two hours (126 minutes).

Figure 6:
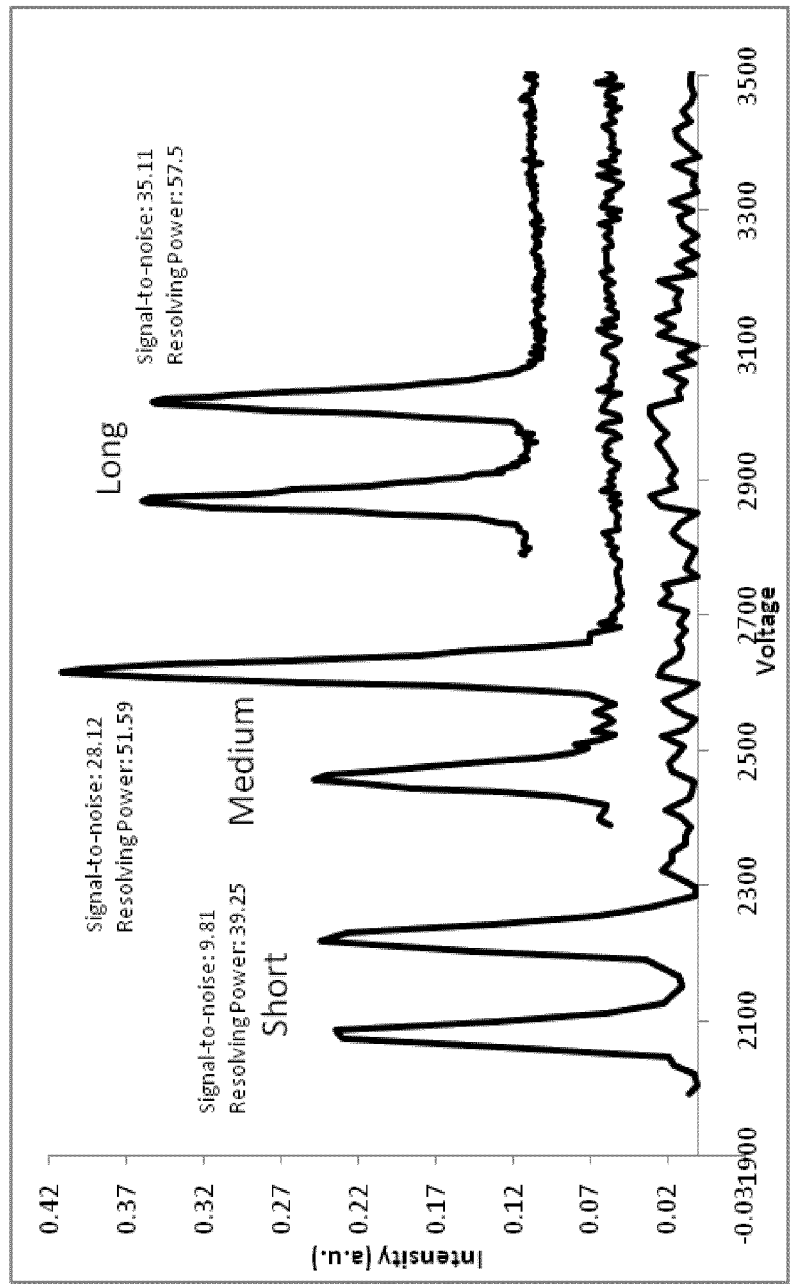
FIG. 6 is an intensity versus drift time plot for 2,4-lutidine at different scan times during an experiment in accordance with embodiments of the present technology.

FIG. 6 shows voltage sweep spectra for 2,4-lutidine for each of these scan times. As shown in FIG. 6, the signal-to-noise ratios for these spectra increased as the scan time increased. However, from the medium scan to the long scan, an increase of only 25% was observed, whereas the short to medium scan gave a signal-to-noise increase of 185%. The decreased resolving powers for the short and medium scans were believed to be caused by the decreased number of data points in these spectra. By reducing the number of data points available, a point-to-point averaging effect was induced, causing the peak to broaden.

In certain embodiments, a complete voltage sweep may be used. In other embodiments, the voltage/drift time curve can be selected based on regions of interest, based on desired peaks. For example, the reactant ion peak may not be of interest when other peaks are present, so the region of the voltage/drift time curve that contains only the reactant ions can be skipped.

System Characterization Through Voltage Sweep.

Figure 7:
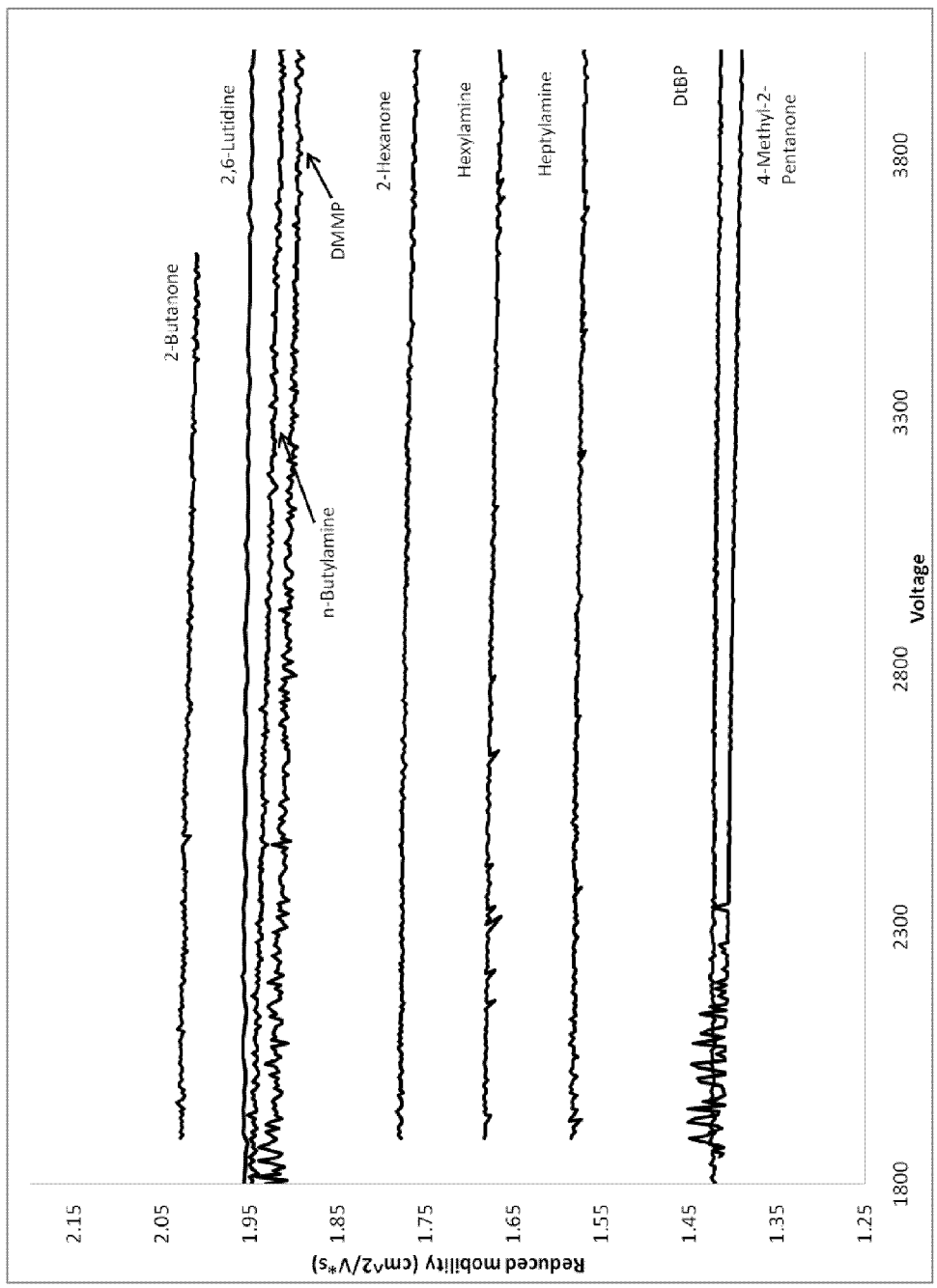
FIG. 7 is a reduced mobility versus voltage plot for certain compounds used in experiments in accordance with embodiments of the present technology.

Using the voltage sweep technique allowed rapid system and compound characterization without the need for multiple experiments. FIG. 7 shows the reduced mobility values for several compounds characterized. The values shown in Table 1 indicate the reduced mobility values calculated for at the optimal voltage or drift time, whereas FIG. 7 shows the reduced mobility calculated for each point along the voltage axis. As a result, a single experiment is needed using the voltage sweep technique instead of several independent spectral acquisitions to produce reduced mobility values across a voltage range.

As shown in FIG. 7, there is an apparent slope of the reduced mobility verses voltage of some of the compounds, e.g., 4-methyl-2-pentanone, DMMP, and n-butylamine. The range in reduced mobility for the compounds was no greater than 0.025 $cm^2V^{-1}s^{-1}$, well within the expected error of ±0.04 $cm^2V^{-1}s^{-1}$. Thus, this was most likely due to a change in atmospheric pressure over the course of the experiment or some other conditions that could not be controlled. However, this technique allowed more accurate measurement of reduced mobility values as compared to a single drift time measurement, as the series of drift times measured can be plotted against the ratio of drift tube length squared over voltage.

From the foregoing, it will be appreciated that specific embodiments of the disclosure have been described herein for purposes of illustration, but that various modifications may be made without deviating from the disclosure. In addition, many of the elements of one embodiment may be combined with other embodiments in addition to or in lieu of the elements of the other embodiments. Accordingly, the technology is not limited except as by the appended claims.

We claim:

1. A method for performing ion mobility spectrometry, comprising:
   ionizing a sample;
   applying a voltage to a plurality of electrodes to generate an electric field across a drift region;
   applying the generated electric field to the ionized sample in a drift medium in the drift region, thereby moving the ionized sample along the drift region, the applied electric field having a plurality of different strength values with respect to a plurality of periods of time, the individual strength values being generally constant during a corresponding one of the periods of time;
   detecting an ion intensity and a drift time of the ionized sample moving through the drift region under the applied electric field with the plurality of strength values;
   with a processor,
      calculating a target drift time corresponding to the individual strength values based at least in part on a temperature of the drift region and the applied voltage across the drift region; and
      determining a value of the ion intensity that corresponds to the calculated target drift time based on the detected ion intensity and drift time.

2. The method of claim 1 wherein the voltage has a plurality of values that are individually generally constant during a corresponding period of time.

3. The method of claim 1 wherein:
   the voltage has a plurality of values that are individually generally constant during a corresponding period of time; and
   the method further includes determining a plurality of values of the detected ion intensity and the drift time corresponding to the plurality of voltage values.

4. The method of claim 1 wherein:
   the voltage has a plurality of values that are individually generally constant during a corresponding period of time; and
   calculating the target drift time includes:
      calculating the target drift time (topt) corresponding to the individual voltage values as follows:

$$t_{opt} = \frac{273.15}{760} \frac{t_g}{0.0395T} \sqrt{\frac{TV}{0.0395}}$$

where tg is a pulse width of an ion gate, T is a temperature of the drift region, and V is the voltage across the drift region.

5. The method of claim 1 wherein applying the electric field includes:
   determining whether the applied voltage is less than a voltage threshold;
   in response to determining that the voltage is less than the voltage threshold, incrementing the voltage by a predetermined amount and detecting an ion intensity and a drift time of the ionized sample moving through the drift region; and in response to determining that the voltage is not less than the voltage threshold, determining a plurality of values of the detected ion intensity and the drift time corresponding to the plurality of voltage values.

6. The method of claim 1 wherein applying the electric field includes:

determining whether the applied voltage is less than a voltage threshold;

in response to determining that the voltage is less than the voltage threshold, incrementing the voltage by a predetermined amount and detecting an ion intensity and a drift time of the ionized sample moving through the drift region; and in response to determining that the voltage is not less than the voltage threshold:

calculating the target drift time (topt) corresponding to the individual voltage values as follows:

$$t_{opt} = \frac{273.15}{760} \frac{t_g}{0.0395T} \sqrt{\frac{TV}{0.0395}}$$

where tg is a pulse width of an ion gate, T is a temperature of the drift region, and V is the voltage across the drift region.

7. The method of claim 1 wherein applying the electric field includes:

determining whether the applied voltage is less than a voltage threshold;

in response to determining that the voltage is less than the voltage threshold, incrementing the voltage by a predetermined amount and detecting an ion intensity and a drift time of the ionized sample moving through the drift region; and in response to determining that the voltage is not less than the voltage threshold:

calculating the target drift time (topt) corresponding to a voltage value as follows:

$$t_{opt} = \frac{273.15}{760} \frac{t_g}{0.0395T} \sqrt{\frac{TV}{0.0395}}$$

where tg is a pulse width of an ion gate, T is a temperature of the drift region, and V is the voltage across the drift region;

determining if additional voltage values exist; and in response to determining that additional voltage values exist, modifying the voltage value and repeating the calculating and determining stages.

8. An ion mobility spectrometry system, comprising:
an ionization section;
a drift tube coupled to the ionization section;
an electric field generator operatively coupled to the drift tube, the electric field generator being configured to generate a generally uniform electric field in the drift tube; and
a controller operatively coupled to the electric field generator, the controller having a non-transitory computer-readable storage medium containing instruction for performing a method comprising:
ionizing a sample in the ionization section;
generating an electric field with the electric field generator;
applying the generated electric field to the ionized sample in the gas phase, thereby moving the ionized sample along a drift region, the applied electric field having a plurality of different strength values with respect to a plurality of periods of time, the individual strength values being generally constant during a corresponding one of the periods of time;
detecting an ion intensity and a drift time of the ionized sample moving through the drift region under the applied electric field with the plurality of strength values;
calculating a target drift time corresponding to the individual strength values based at least in part on a temperature of the drift region and the applied voltage across the drift region; and
determining a value of the ion intensity that corresponds to the calculated target drift time based on the detected ion intensity and drift time.

9. The ion mobility spectrometry system of claim 8 wherein:
the electric field generator includes a plurality of electrodes; and
generating the electric field includes applying the voltage to the plurality of electrodes, and wherein the voltage has a plurality of values that are individually generally constant during a corresponding period of time.

10. The ion mobility spectrometry system of claim 8 wherein:
the electric field generator includes a plurality of electrodes;
generating the electric field includes applying the voltage to the plurality of electrodes, and wherein the voltage has a plurality of values that are individually generally constant during a corresponding period of time; and
the method further includes determining a plurality of values of the detected ion intensity and the drift time corresponding to the plurality of voltage values.

11. The ion mobility spectrometry system of claim 8 wherein:
the electric field generator includes a plurality of electrodes;
generating the electric field includes applying the voltage to the plurality of electrodes, and wherein the voltage has a plurality of values that are individually generally constant during a corresponding period of time; and
calculating the target drift time includes:
calculating the target drift time (topt) corresponding to the individual voltage values as follows:

$$t_{opt} = \frac{273.15}{760} \frac{t_g}{0.0395T} \sqrt{\frac{TV}{0.0395}}$$

where tg is a pulse width of an ion gate, T is a temperature of the drift region, and V is the voltage across the drift region.

12. The ion mobility spectrometry system of claim 8 wherein applying the electric field includes:
applying the voltage to generate the electric field;
determining whether the applied voltage is less than a voltage threshold;
in response to determining that the voltage is less than the voltage threshold, incrementing the voltage by a predetermined amount and detecting an ion intensity and a drift time of the ionized sample moving through the drift region; and in response to determining that the voltage is not less than the voltage threshold, determining a plurality of values of the detected ion intensity and the drift time corresponding to the plurality of voltage values.

13. The ion mobility spectrometry system of claim 8 wherein applying the electric field includes:
applying the voltage to generate the electric field;
determining whether the applied voltage is less than a voltage threshold;
in response to determining that the voltage is less than the voltage threshold, incrementing the voltage by a predetermined amount and detecting an ion intensity and a drift time of the ionized sample moving through the drift region; and
in response to determining that the voltage is not less than the voltage threshold:
calculating the target drift time (topt) corresponding to the individual voltage values as follows:

$$t_{opt} = \frac{273.15}{760} \frac{t_g}{0.0395T} \sqrt{\frac{TV}{0.0395}}$$

where tg is a pulse width of an ion gate, T is a temperature of the drift region, and V is the voltage across the drift region.

14. The ion mobility spectrometry system of claim 8 wherein applying the electric field includes:
applying the voltage to generate the electric field;
determining whether the applied voltage is less than a voltage threshold;
in response to determining that the voltage is less than the voltage threshold, incrementing the voltage by a predetermined amount and detecting an ion intensity and a drift time of the ionized sample moving through the drift region; and
in response to determining that the voltage is not less than the voltage threshold:
calculating the target drift time (topt) corresponding to a voltage value as follows:

$$t_{opt} = \frac{273.15}{760} \frac{t_g}{0.0395T} \sqrt{\frac{TV}{0.0395}}$$

where tg is a pulse width of an ion gate, T is a temperature of the drift region, and V is the voltage across the drift region;
determining if additional voltage values exist; and
in response to determining that additional voltage values exist, modifying the voltage value and repeating the calculating and determining stages.

15. A computer system for use in an ion mobility spectrometry system, comprising:
a processor;
a non-transitory computer-readable storage medium operatively coupled to the processor, the computer-readable storage medium containing instructions for performing a method comprising:
applying an electric field to an ionized sample in a drift medium, thereby moving the ionized sample along a drift region;
adjusting the applied electric field to have a plurality of different strength values with respect to time;
detecting an ion intensity and a drift time of the ionized sample moving through the drift region under the applied electric field with the plurality of strength values;
calculating a target drift time corresponding to the individual strength values based at least in part on a temperature of the drift region and a voltage across the drift region; and
determining a value of the ion intensity that corresponds to the calculated target drift time based on the detected ion intensity and drift time.

16. The computer system of claim 15 wherein:
applying an electric field includes applying a voltage to a plurality of electrodes to generate the electric field;
the voltage has a plurality of values that are individually generally constant during a corresponding period of time; and
the method further includes determining a plurality of values of the detected ion intensity and the drift time corresponding to the plurality of voltage values.

17. The computer system of claim 15 wherein:
applying the electric field includes applying a voltage to a plurality of electrodes to generate the electric field; and
calculating the target drift time includes:
calculating the target drift time (topt) corresponding to the individual voltage values as follows:

$$t_{opt} = \frac{273.15}{760} \frac{t_g}{0.0395T} \sqrt{\frac{TV}{0.0395}}$$

where tg is a pulse width of an ion gate, T is a temperature of the drift region, and V is the voltage across the drift region.

18. The computer system of claim 15 wherein applying the electric field includes:
applying a voltage to generate the electric field;
determining whether the applied voltage is less than a voltage threshold;
in response to determining that the voltage is less than the voltage threshold, incrementing the voltage by a predetermined amount and detecting an ion intensity and a drift time of the ionized sample moving through the drift region; and
in response to determining that the voltage is not less than the voltage threshold, determining a plurality of values of the detected ion intensity and the drift time corresponding to the plurality of voltage values.

19. The computer system of claim 15 wherein applying the electric field includes:
applying a voltage to generate the electric field;
determining whether the applied voltage is less than a voltage threshold;
in response to determining that the voltage is less than the voltage threshold, incrementing the voltage by a predetermined amount and detecting an ion intensity and a drift time of the ionized sample moving through the drift region; and
in response to determining that the voltage is not less than the voltage threshold:
calculating the target drift time (topt) corresponding to the individual voltage values as follows:

$$t_{opt} = \frac{273.15}{760} \frac{t_g}{0.0395T} \sqrt{\frac{TV}{0.0395}}$$

where tg is a pulse width of an ion gate, T is a temperature of the drift region, and V is the voltage across the drift region.

20. The computer system of claim 15 wherein applying the electric field includes:
   applying a voltage to generate the electric field;
   determining whether the applied voltage is less than a voltage threshold;
   in response to determining that the voltage is less than the voltage threshold, incrementing the voltage by a predetermined amount and detecting an ion intensity and a drift time of the ionized sample moving through the drift region; and
   in response to determining that the voltage is not less than the voltage threshold:
   calculating the target drift time (topt) corresponding to a voltage value as follows:

$$t_{opt} = \frac{273.15}{760} \frac{t_g}{0.0395T} \sqrt{\frac{TV}{0.0395}}$$

where tg is a pulse width of an ion gate, T is a temperature of the drift region, and V is the voltage across the drift region;
   determining if additional voltage values exist; and
   in response to determining that additional voltage values exist, modifying the voltage value and repeating the calculating and determining stages.

21. A non-transitory computer-readable storage medium for use in an ion mobility spectrometry system having a drift tube, an ion gate configured to admit an ionized sample into the drift tube, and an electric field generator configured to generate an electric field in the drift tube upon application of an electrical voltage, wherein the computer-readable storage medium contains instructions that, when executed by one or more processors, causing the one or more processors to perform a process comprising:
   collecting data of ion intensity and drift time of the ionized sample moving through the drift tube under the electric field upon application of an electrical voltage to the electric field generator, the electrical voltage having a plurality of voltage values (V) with respect to time;
   calculating a target drift time (topt) corresponding to at least one of the voltage values (V) of the applied electrical voltage as follows:

$$t_{opt} = \frac{273.15}{760} \frac{t_g}{0.0395T} \sqrt{\frac{TV}{0.0395}}$$

where tg is a pulse width of the ion gate and T is a temperature in the drift tube;
   determining a value of the ion intensity that corresponds to the calculated target drift time from the collected data of the ion intensity and drift time; and
   analyzing the determined value of the ion intensity and the target drift time to identify a composition of the ionized sample.

22. The computer-readable storage medium of claim 21 wherein:
   calculating the target drift time ($t_{opt}$) includes calculating a plurality of target drift times ($t_{opt}$) individually corresponding to one of a plurality of the voltage values (V) of the applied electrical voltage; and
   determining the value of the ion intensity includes determining a value of the ion intensity individually corresponding to one of the plurality of calculated target drift times from the collected data of the ion intensity and drift time.

23. The computer-readable storage medium of claim 21 wherein:
   calculating the target drift time ($t_{opt}$) includes calculating a plurality of target drift times ($t_{opt}$) individually corresponding to one of a plurality of the voltage values (V) of the applied electrical voltage;
   determining the value of the ion intensity includes determining a value of the ion intensity individually corresponding to one of the plurality of calculated target drift times from the collected data of the ion intensity and drift time; and
   analyzing the determined value of the ion intensity and the target drift time includes identifying the composition of the ionized sample based on the determined plurality of values of ion intensity and corresponding target drift times.

* * * * *